(12) United States Patent
Remondini

(10) Patent No.: US 10,695,718 B2
(45) Date of Patent: Jun. 30, 2020

(54) MEASURING APPARATUS HAVING A DEVICE FOR GENERATING CLEAN AIR

(71) Applicant: SACMI COOPERATIVA MECCANICI IMOLA SOCIETA' COOPERATIVA, Imola (Bologna) (IT)

(72) Inventor: Marco Remondini, Imola (IT)

(73) Assignee: SACMI COOPERATIVA MECCANICI IMOLA SOCIETA' COOPERATIVA, Imola (IT)

( * ) Notice: Subject to any disclaimer, the term of this patent is extended or adjusted under 35 U.S.C. 154(b) by 351 days.

(21) Appl. No.: 15/568,759

(22) PCT Filed: May 13, 2016

(86) PCT No.: PCT/IB2016/052762
§ 371 (c)(1),
(2) Date: Oct. 23, 2017

(87) PCT Pub. No.: WO2016/181353
PCT Pub. Date: Nov. 17, 2016

(65) Prior Publication Data
US 2018/0078899 A1 Mar. 22, 2018

(30) Foreign Application Priority Data

May 13, 2015 (IT) .............. BO2015A0246

(51) Int. Cl.
*A61L 9/00* (2006.01)
*G01N 21/00* (2006.01)
(Continued)

(52) U.S. Cl.
CPC ......... *B01D 53/869* (2013.01); *B01D 53/864* (2013.01); *B01D 53/88* (2013.01);
(Continued)

(58) Field of Classification Search
CPC ........ A61L 9/00; A61L 9/02; A61L 2209/111; A61L 2209/15; A61L 2209/21; B01D 53/34; G01N 33/0022
(Continued)

(56) References Cited

U.S. PATENT DOCUMENTS 4,884,435 A 12/1989 Ehara
5,134,080 A 7/1992 Bell et al.
(Continued)

FOREIGN PATENT DOCUMENTS

DE 3929521 A1 * 3/1991 ............. B01D 53/86
DE 3929521 A1 3/1991
(Continued)

OTHER PUBLICATIONS

European Patent Office Machine English Translation of the Description and the Claims Sections of DE-3929521-A1.*

*Primary Examiner* — Monzer R Chorbaji
(74) *Attorney, Agent, or Firm* — Pearne & Gordon LLP

(57) ABSTRACT

A device (1) for generating clean air in a measuring apparatus, comprising:
a duct (2) having an inlet and an outlet for the passage of an air flow to be cleaned;
a platinum wire (3), positioned inside the duct (2), for intercepting the air flow to be cleaned, the platinum wire (3) is inserted in an electrical circuit (17) connectable to an electricity supply (15) to be operatively crossed by an electrical current.

12 Claims, 3 Drawing Sheets

(51) Int. Cl.
*G01N 25/00* (2006.01)
*B01D 53/86* (2006.01)
*G01N 33/00* (2006.01)
*B01D 53/88* (2006.01)

(52) U.S. Cl.
CPC ....... *B01D 53/885* (2013.01); *G01N 33/0009* (2013.01); *B01D 2255/1021* (2013.01); *B01D 2257/708* (2013.01); *B01D 2257/90* (2013.01); *B01D 2258/06* (2013.01); *G01N 33/0029* (2013.01)

(58) Field of Classification Search
USPC .............. 422/3–4, 307; 73/1.02, 19.01, 23.2, 73/25.01, 863
See application file for complete search history.

(56) References Cited

U.S. PATENT DOCUMENTS

| | | | |
|---|---|---|---|
| 5,158,654 A | 10/1992 | Yoshimoto et al. | |
| 6,338,266 B1* | 1/2002 | Warburton | G01N 13/00 205/775 |
| 8,256,264 B2 | 9/2012 | Bosi et al. | |
| 2010/0300180 A1* | 12/2010 | Bosi | G01N 33/0006 73/29.02 |
| 2012/0279277 A1 | 11/2012 | Parusel et al. | |

FOREIGN PATENT DOCUMENTS

| | | |
|---|---|---|
| EP | 03317299 A2 | 5/1989 |
| EP | 03398766 A1 | 11/1990 |
| WO | 0240839 A1 | 5/2002 |
| WO | 2009068965 A1 | 6/2009 |

\* cited by examiner

MEASURING APPARATUS HAVING A DEVICE FOR GENERATING CLEAN AIR

TECHNICAL FIELD

This invention relates to a measuring apparatus having a device for generating clean air.

More specifically, this invention relates to a device and a method for generating clean air for a measuring apparatus, for example an electronic nose. Moreover, the invention also covers the measuring apparatus equipped with the device for generating air clean.

BACKGROUND ART

As is known, electronic noses are instruments which allow continuously analysing the ambient air. Electronic noses are capable of classifying the quality of a gas coming from an environment to assign a specific olfactory class or to olfactarily quantify the gas analysed, by assigning an olfactory class to the gas and estimating its odour concentration.

The operation of the electronic nose follows that of the human olfactory system and is generally divided into steps:
measuring the gas using suitable sensors;
processing the signals coming from the sensors;
recognising the odours;

The electronic noses comprise an intake duct, which connects the outside environment with a measuring chamber. The circulation of the gas through the electronic nose is usually guaranteed by a suction device. The suction device may be, for example, a pump or a fan.

The measuring chamber, which is usually made of a chemically inert material, houses a matrix of sensors. The calibration of the sensors of the electronic nose is performed using the passage of a reference gas (usually air) inside the measuring chamber, in such a way as to establish a baseline for the response of the sensors.

Electronic noses, like other measuring apparatuses, for example gas chromatograph equipment, require a source of clean air, that is odourless air, such as zero air; the clean air may serve for example to generate a reference odour by mixing the clean air together with molecules of butanol, or to regulate a humidity level of the air inside the measuring apparatus.

Often, in measuring apparatuses requiring clean air, the latter is supplied by a cylinder integrated in the apparatus.

However, this solution has the drawback of increasing the size and cost of the apparatus. Moreover, the use of a cylinder has problems linked to maintenance and replacement, thus not providing the best practical and safety conditions.

Alternatively, measuring apparatuses requiring clean air have a device on board for generating the air clean.

In order to generate clean air, in the context of small devices that can be used on board a measuring apparatus (such as for example an electronic nose), the prior art teaches the use of catalytic oxidisers.

These catalytic oxidisers normally use the oxides of precious metals (for example platinum or palladium) as catalysers and comprise a furnace for heating the infeed air.

However, this solution also has drawbacks, mainly associated with the fact that it requires increased energy, with consequent increases in the management costs.

Examples of devices to generate clean air can be found in the following patent documents: DE3929521A1, EP0398766A1, WO2009/068965A1, U.S. Pat. No. 5,134, 080A, EP0317299A2, US20121279227. However, these documents do not provide effective solutions applied particularly to measurement apparatuses, such as in particular electronic noses.

DISCLOSURE OF THE INVENTION

The aim of this disclosure is to provide a measuring apparatus having a device for generating clean air in a measuring apparatus that overcome the above-mentioned drawbacks of the prior art.

More specifically, the aim of this disclosure is to provide a device and a method for generating clean air in a measuring apparatus, which allows maintaining particularly small sizes.

The present disclosure provides a device and a method for generating clean air in a measuring apparatus, which are particularly energy efficient and affordable to manage.

These aims are fully achieved by the measuring apparatus according to this disclosure as characterised in the appended claims.

More specifically, the device for generating clean air for a measuring apparatus comprises a duct, elongate according to a longitudinal direction.

The duct has an inlet and an outlet for the passage of a flow of air to be cleaned.

The inlet of the duct is designed to receive an infeed flow of air to be cleaned. The outlet of the duct is designed to make available a corresponding flow of clean air.

A platinum wire designed to intercept a flow of air to be cleaned is positioned inside the duct.

The platinum wire is inserted in the electrical circuit. The electrical circuit is (operatively) connected (that is connectable) to an electricity supply to be operatively crossed by an electrical current.

With this solution, it is no longer necessary to heat the air inside the duct, which in turn leads to the heating of the platinum wire and the following release of molecules into the air flow. According to this technical solution, the platinum wire is heated directly by the passage of a current, with considerable saving of energy and volumes.

Furthermore, the wire is positioned along a path extending from the inlet to the outlet of the duct.

The aforementioned platinum wire is positioned about the supporting rod, thus defining a helical path that extends along the longitudinal direction. This solution advantageously makes it possible to use a larger quantity of platinum wire inside the duct, so as to maximise the effect of catalytic oxidisation.

Given the helical winding of the wire inside the duct, the device also comprises a supporting rod positioned inside the duct, about which the platinum wire is wound, and made for example, of alumina.

In addition to allowing the helical winding of the wire about it, the supporting rod also guarantees that the above-mentioned wire is not subjected to bending and does not come in contact with the walls of the duct.

The device also comprises an infeed nozzle, which is positioned at the inlet of the duct, for introducing air to be cleaned into the duct, together with an outfeed nozzle positioned at the outlet of the duct, for extracting the clean air from the duct.

Advantageously, the infeed nozzle and the outfeed nozzle are made of an electrical conductor material and are connected to the platinum wire to form part of the electrical circuit and to allow the passage of the current from the inlet of the duct towards the outside of the duct.

Preferably, the infeed and the outfeed nozzle have respective fastening portions projecting inside the duct.

The supporting rod, which is positioned inside the duct to support the platinum wire, has a first and a second end connected to the fastening portions of the first and of the second nozzle.

According to a further aspect, this disclosure further relates to a measuring apparatus comprising a device for generating clean air.

Preferably, the apparatus comprises a measuring chamber and an intake duct having two ends, an inlet end in communication with the outside environment and an outlet end connected with the measuring chamber. The apparatus further comprises at least one sensor, positioned inside the measuring chamber and designed to detect olfactory properties of a gas. In addition, there is a control unit designed to process signals coming from the sensor and to provide a parameter representing the odours measured in the gas. A suction device is designed to circulate gas in the measuring chamber.

Preferably, the device for generating clean air is positioned along the intake duct in such a way that the duct is crossed by an air flow coming from the outside environment and is directed towards the measuring chamber.

According to a first embodiment, the apparatus comprises a further intake duct having two ends, an inlet end in communication with the outside environment and an outlet end connected with the measuring chamber.

Preferably, the apparatus comprises a cleaning device designed to clean the further intake duct and the measuring chamber of olfactory residues, in order to restore the properties of the sensor following a measurement. The cleaning device is designed to generate a flow of ozone inside the intake duct and the measuring chamber.

According to a further aspect, this disclosure relates to a method for generating clean air for a measuring apparatus, comprising the following steps:

- introducing air to be cleaned into a duct having an inlet and an outlet;
- interaction of the air inside the duct with a platinum wire to generate a catalytic oxidation with circulation of an electrical current in the platinum wire;
- emission of clean air through the outlet of the duct.

Preferably, the air introduced into the duct is at ambient temperature.

BRIEF DESCRIPTION OF DRAWINGS

This and other features of the disclosure will become more apparent from the following detailed description of a preferred, non-limiting example embodiment of it, with reference to the accompanying drawings, in which.

DETAILED DESCRIPTION OF PREFERRED EMBODIMENTS OF THE INVENTION

Figure 1:
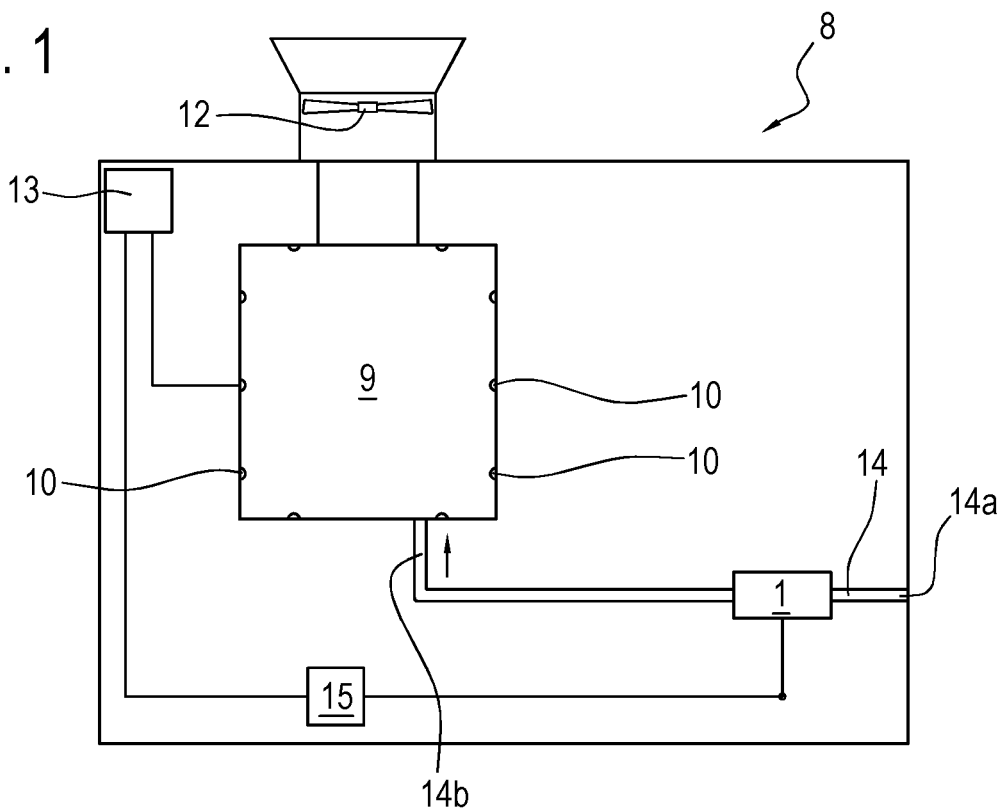
FIG. 1 shows a schematic view of the apparatus for generating clean air according to a first embodiment.

With reference to the accompanying drawings, the numeral 1 denotes a device for generating clean air.

More specifically, the device 1 relates to a measuring apparatus, usually an electronic nose.

The present description regards a measurement apparatus (for example, an electronic nose) that includes said device 1. In addition, the present description also regards the device 1 per se, applicable to a measuring apparatus (for example an electronic nose).

The device 1 comprises a duct 2. The duct 2 has an inlet and an outlet for allowing the passage of a flow of air to be cleaned and made odourless. In other words, the air to be cleaned enters the duct 2 from the inlet and exits clean from the outlet.

The device 1 also comprises a wire 3 made of platinum, or of another material designed to generate catalytic oxidisation. The material forming the wire 3 is an electrical conductor material.

The wire is positioned inside the duct 2, according to a preferably helical winding; in this way, the air flow crossing the duct touches the wire 3.

Operatively, the wire 3 is heated by a current crossing it; in this way the wire 3 releases particles into the duct 2, which detach from the wire and form a deposit on the inner surface of the pipe, thus heating the air flow inside the duct 2 and cleaning the dirty air by a process defined as catalytic oxidisation.

The wire 3 is part of an electrical circuit 17 having a generator 15 designed to circulate an electrical current in the wire 3.

Thus, the device 1 comprises a heating element designed to heat the wire 3; the heating element consists of the electrical circuit 17 and of the current generated in it.

The duct 2 is elongate from the inlet to the outlet along a longitudinal direction and the wire 3 is positioned along a path extending from the inlet to the outlet of the duct 2.

Figure 5:
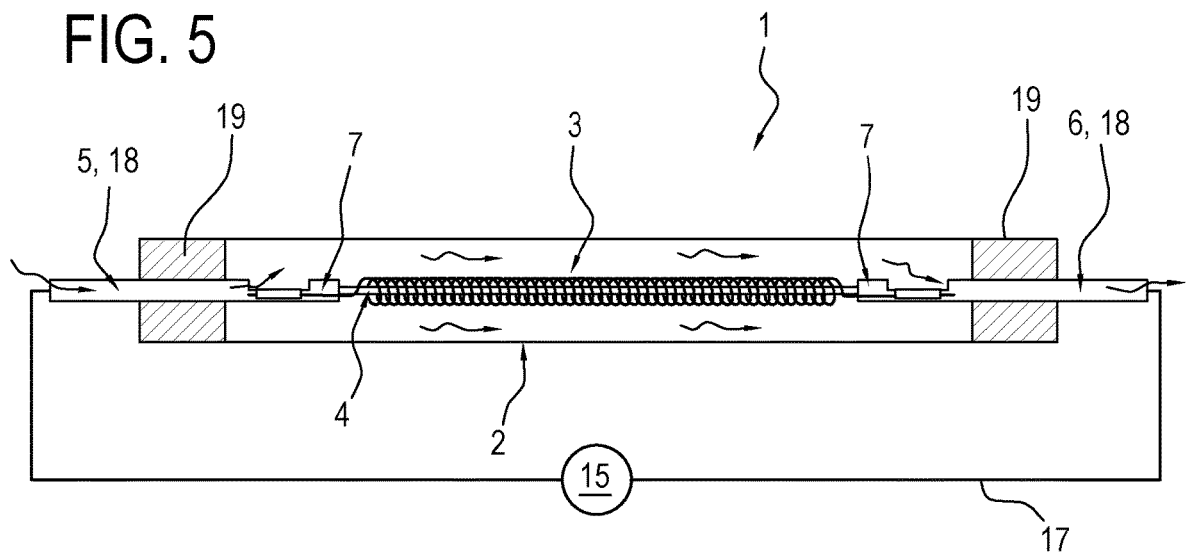
FIG. 5 shows a schematic side view of the device for generating clean air according to a first embodiment.

In an example embodiment (reference may be made for example to FIG. 5), the device 1 comprises a supporting rod 4 positioned inside the duct and designed to support the wire 3. The wire 3 is positioned about the supporting rod 4, thus defining a helical path that extends along the longitudinal direction. The wire must be folded in spiral or helical shape, in order to be housed inside the pipe without touching its walls.

The supporting rod 4 is preferably made of alumina.

The device 1 for generating clean air comprises an infeed nozzle 5 positioned at the inlet of the duct, for introducing air to be cleaned into the duct, and an outfeed nozzle 6 positioned at the outlet of the duct, for extracting the clean air from the duct 2. The nozzles are made of an electrical conductor material and are connected to the wire 3 to form part of the electrical circuit 17 and to thus allow the current to pass to and from the outside of the duct 2.

In this embodiment, the infeed nozzle 5 and the outfeed nozzle 6 have respective fastening portions 7 projecting inside the duct 2.

The device 1 comprises a supporting rod 4 positioned inside the duct 2 to support the wire 3, which has a first and a second end connected to the fastening portions 7 of the infeed nozzle 5 and of the outfeed nozzle 6, respectively.

In addition to supporting the rod, the fastening portions 7 also act as terminals 18 for operatively closing the electrical circuit 17 and allowing the current to cross the wire 3.

The infeed nozzle 5 and the outfeed nozzle 6 are perforated and are inserted in appropriate perforated caps 19, which are suitably shaped to adapt to the ends of the duct 2.

In a further embodiment example (illustrated by way of example in FIG. 6), the infeed nozzle 5 and the outfeed nozzle 6 do not have respective projecting fastening portions.

The infeed nozzle 5 and the outfeed nozzle 6 are positioned along an axis transversal to the direction of longitudinal extension of the duct 2. They protrude from the bottom or top along the aforementioned axis transversal to the longitudinal direction of extension of the duct 2.

Figure 6:
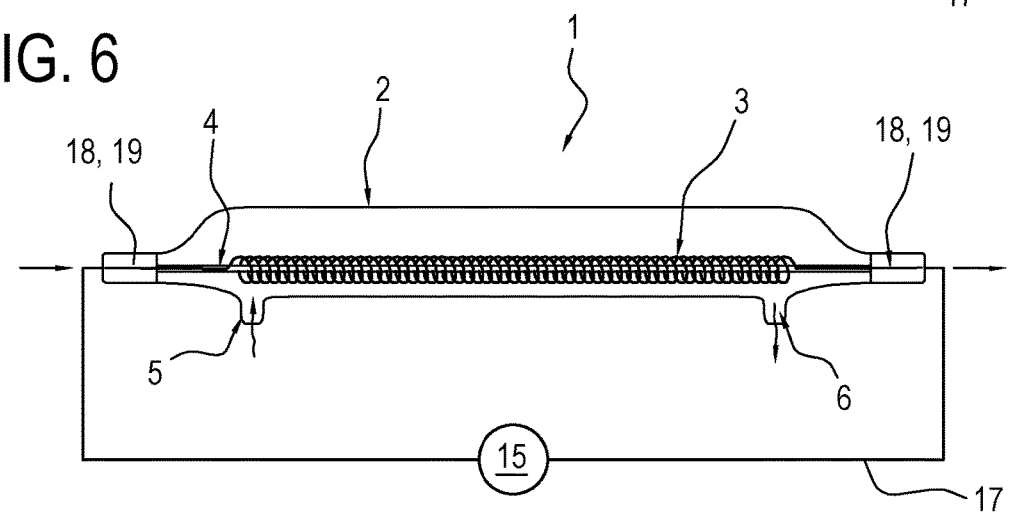
FIG. 6 shows a schematic side view of the device for generating air clean according to a further embodiment.
Figure 7A:
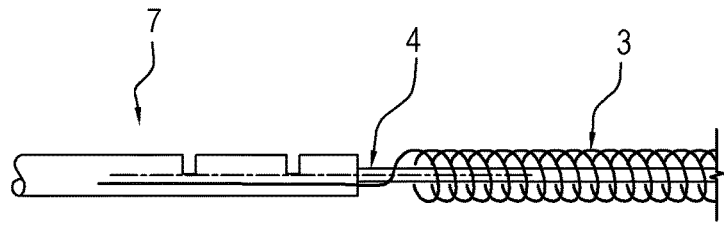
FIG. 7A is a schematic view of a detail of the projecting fastening portions of the device for generating clean air from FIG. 1, in the open configuration.
Figure 7B:
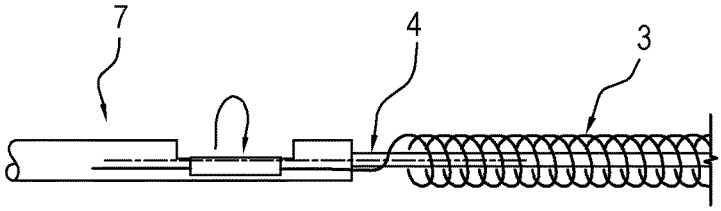
FIG. 7B is a schematic view of a detail of the projecting fastening portions of the device for generating clean air from FIG. 1, in the closed configuration.

In the example illustrated in FIG. 6, the device 1 for generating clean air has a further inlet and a further outlet, positioned at the two ends of the duct 2 along the longitudinal direction of extension.

The platinum wire 3 is connectable to an electricity supply 15 by the respective portions of wire that protrude from the further inlet and from the further outlet of the duct 2.

According to this embodiment example, the inlet and the outlet ends of the duct 2 act as terminals 18, for operatively closing the electrical circuit 17 and allowing the circulation of the electrical current designed to heat the wire 3.

The duct 2 is closed at the ends by respective perforated caps 19 to allow the respective insertion and the respective removal of the wire 3 from the duct 2, which is operatively connected to the electricity supply 15.

In accordance with this disclosure, a measuring apparatus 8 is defined comprising the device 1 for generating clean air described above.

The aforementioned apparatus 8 is an electronic nose comprising:
 a measuring chamber 9;
 an intake duct 11 having a first inlet end 11a in communication with the outside environment and an outlet end 11b connected with the measuring chamber;
 at least one olfactory sensor 10, positioned inside the measuring chamber 9 and designed to detect olfactory properties of a gas;
 a control unit 13 connected to an electricity supply 15 and designed to process signals coming from the at least one sensor 10 and to provide a parameter representing the odours measured in the gas;
 a suction device 12 designed to circulate the gas in the measuring chamber 9.

More in detail, the apparatus 8 comprises a cleaning device 16 positioned on board the machine and designed to clean the intake duct 11 and the measuring chamber 9 of olfactory residues.

The cleaning device 16 is operatively connected to the electricity supply 15 and is designed to generate a flow of ozone inside the intake duct 11 and the measuring chamber 9.

Thus, the cleaning device 16 is also defined as an ozone generator. The ozone generator may be operatively connected to the electricity supply 15 or to another supply, for example a voltage generator.

According to a first embodiment, illustrated in FIG. 1, an apparatus 8 is defined in which the device 1 for generating clean air is positioned along a further intake duct 14.

In this way, the unclean air coming from the outside environment enters from a second inlet end 14a, passes through the device 1 and exits clean from a second outlet end 14b, which is connected to a measuring chamber 9. The device 1 is operatively connected to the electricity supply 15.

Figure 2:
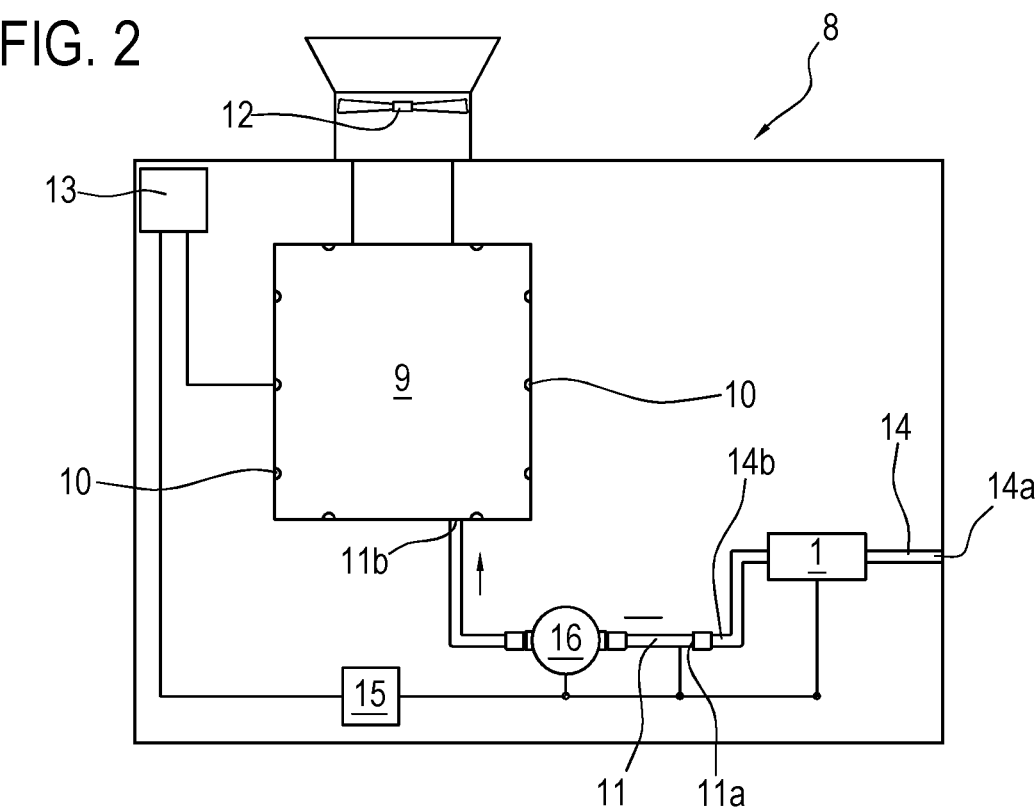
FIG. 2 shows a schematic view of the apparatus for generating clean air according to yet another embodiment.

According to a further embodiment, illustrated by way of example in FIG. 2, an apparatus 8 is defined in which the device 1 for generating clean air is positioned along a further intake duct 14, so that the unclean air coming from the outside environment enters a second inlet end 14a and exits clean from a second outlet end 14b. In this embodiment, the second outlet end 14b is operatively connected with the first inlet end 11a of the intake duct 11. The exchange of the infeed air of the intake duct 11 is regulated by a valve. In this way, the device 1 for generating clean air is operatively connected to a cleaning device 16, for example an ozone generator. Both are connected to an electricity supply 15.

Figure 3:
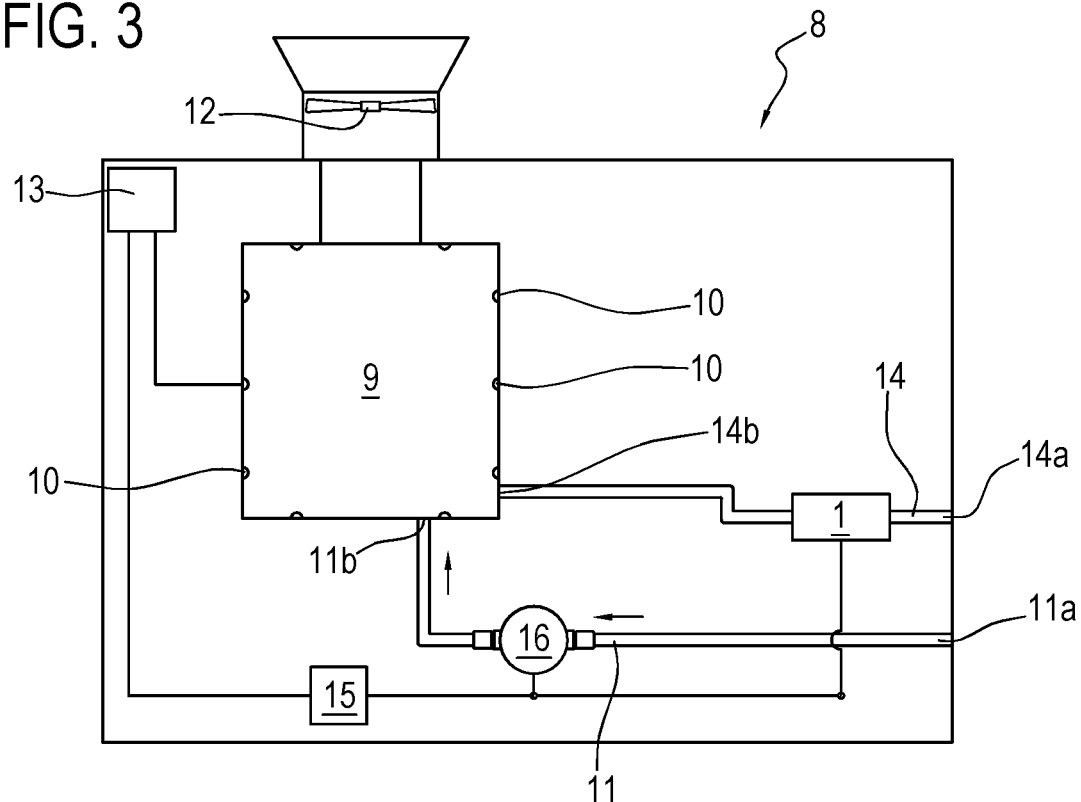
FIG. 3 shows a schematic view of the apparatus for generating clean air according to yet another embodiment.

According to a further embodiment, illustrated in turn in FIG. 3, the aforesaid apparatus comprises a further intake duct 14 having a second inlet end 14a in communication with the outside environment and a second outlet end 14b connected with the measuring chamber 9, and in which the device 1 for generating clean air is positioned along the mentioned further intake duct 14, which is connectable to the electricity supply 15.

Figure 4:
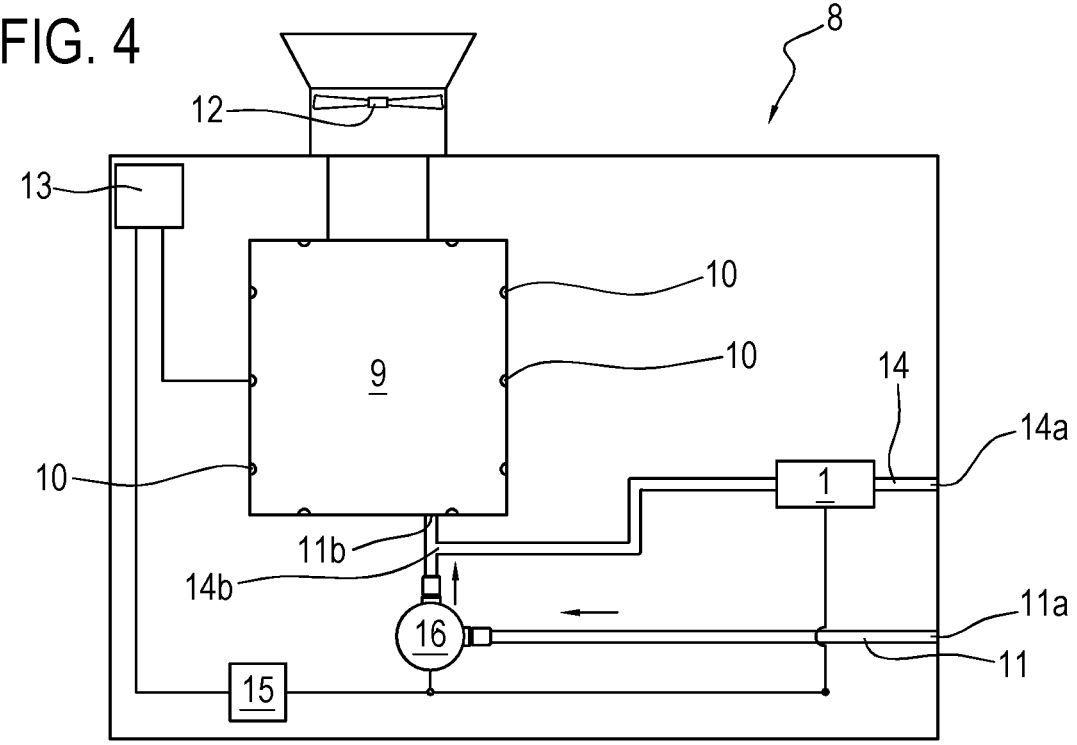
FIG. 4 shows a schematic view of the apparatus for generating clean air according to yet another embodiment.

According to a further embodiment, illustrated in FIG. 4, the apparatus 8 comprises a further intake duct 14 having a second inlet end 14a in communication with the outside environment and a second outlet end 14b operatively connected to the intake duct 11 by a valve, that is merging into the intake duct 11. According to this embodiment, the device 1 for generating clean air is positioned along the further intake duct 14, that is between the second inlet end 14a and the second outlet end 14b.

According to this disclosure, a method is also defined for generating clean air for a measuring apparatus, comprising the steps of:
 introducing air to be cleaned into a duct 2 having an inlet and an outlet;
 interaction of the air inside the duct with a platinum wire 3 to generate a catalytic oxidation;
 emission of clean air through the outlet of the duct 2,
the method being characterised in that it comprises a circulation of an electrical current in the platinum wire 3.

Furthermore, the air introduced into the duct 2 is preferably at ambient temperature.

The invention claimed is:

1. A measuring apparatus including a device for generating clean air for the measuring apparatus, wherein the device comprises:
 a duct having an inlet, designed to receive an infeed flow of air to be cleaned, and an outlet for making available a corresponding flow of clean air;
 a platinum wire, positioned inside the duct, for intercepting the air flow to be cleaned, wherein the platinum wire is inserted in an electrical circuit connectable to an electricity supply to be operatively crossed by an electrical current;
 a supporting rod positioned inside the duct for supporting the platinum wire, wherein the supporting rod includes a portion elongating from a first end to a second end, the second end being spaced from the first end,
and wherein the platinum wire includes a wire portion wound about said portion of the supporting rod, to define a plurality of turns of the platinum wire, the turns being located around said portion of the supporting rod.

2. The measuring apparatus according to claim 1, wherein the duct is elongate from the inlet to the outlet along a longitudinal direction and the wire is positioned along a path extending from the inlet to the outlet of the duct.

3. The measuring apparatus device according to claim 2, wherein the wire defines an helical path that extends along the longitudinal direction.

4. The measuring apparatus according to claim 3, wherein the supporting rod is made of alumina.

5. The measuring apparatus according to claim 1, comprising:
   an infeed nozzle positioned at the inlet of the duct, for introducing air to be cleaned into the duct;
   an outfeed nozzle positioned at the outlet of the duct, for extracting clean air from the duct.

6. The measuring apparatus according to claim 5, wherein the infeed nozzle and the outfeed nozzle are made of an electrical conductor material and are connected to the wire to form part of the electrical circuit and to allow the electrical current to pass through the wire.

7. The measuring apparatus according to claim 5, wherein the infeed nozzle and the outfeed nozzle have respective fastening portions projecting inside the duct, and wherein the device comprises a supporting rod, positioned inside the duct to support the wire and having a first and a second end connected to the fastening portions of the first and second nozzle, respectively.

8. The measuring apparatus according to claim 1, wherein the measuring apparatus is an electronic nose comprising:
   a measuring chamber;
   an intake duct having a first inlet end in communication with the outside environment and an outlet end connected with the measuring chamber;
   at least one olfactory sensor, positioned inside the measuring chamber and designed to detect olfactory properties of a gas;
   a control unit connected to an electricity supply and designed to process signals coming from the at least one sensor and to provide a parameter representing the odours measured in the gas;
   a suction device designed to circulate the gas in the measuring chamber.

9. The measuring apparatus according to claim 8, wherein the apparatus comprises a cleaning device positioned on board the machine and designed to clean the intake duct and the measuring chamber of olfactory residues, wherein the cleaning device is operatively connected to the electricity supply and is configured to generate a flow of ozone inside the intake duct and the measuring chamber.

10. The measuring apparatus according to claim 1, wherein the device is arranged inside the measuring apparatus.

11. A method for generating clean air in measuring apparatus, comprising the following steps:
    introducing clean air into a duct having an inlet and an outlet;
    interaction of the air inside the duct with a platinum wire to generate a catalytic oxidation;
    emission of clean air through the outlet of the duct,
   wherein the method further comprises a circulation of an electrical current in the platinum wire, wherein the platinum wire is supported by a supporting rod positioned inside the duct, the supporting rod including a portion elongating from a first end to a second end, the second end being spaced from the first end,
   and wherein the platinum wire includes a wire portion wound about said portion of the supporting rod, to define a plurality of turns of the platinum wire, the turns being located around said portion of the supporting rod.

12. The method according to claim 11, wherein the air introduced into the duct is at ambient temperature.

* * * * *

UNITED STATES PATENT AND TRADEMARK OFFICE
CERTIFICATE OF CORRECTION

PATENT NO. : 10,695,718 B2
APPLICATION NO. : 15/568759
DATED : June 30, 2020
INVENTOR(S) : Marco Remondini It is certified that error appears in the above-identified patent and that said Letters Patent is hereby corrected as shown below:

In the Claims

Column 7, Line 3, Claim 3, after "apparatus" delete "device".

Signed and Sealed this
Twenty-second Day of September, 2020

Andrei Iancu
*Director of the United States Patent and Trademark Office*